United States Patent [19]

Denis et al.

[11] Patent Number: 5,081,292

[45] Date of Patent: Jan. 14, 1992

[54] PREPARATION OF β, γ-UNSATURATED CARBOXYLIC ACIDS

[75] Inventors: Philippe Denis, Decines; Jean Jenck, Chassieu; Robert Perron, Charly, all of France

[73] Assignee: Rhone-Poulenc Chimie, Courbevoie, France

[21] Appl. No.: 516,737

[22] Filed: Apr. 30, 1990

[30] Foreign Application Priority Data

Apr. 28, 1989 [FR] France ................. 89 06019

[51] Int. Cl.⁵ .................................. C07C 51/12
[52] U.S. Cl. ........................... 562/519; 260/413; 560/114; 560/204; 562/406; 562/497; 562/590; 562/595; 562/598
[58] Field of Search ............ 562/406, 497, 519, 590, 562/595, 598; 560/204, 114; 260/413

[56] References Cited

U.S. PATENT DOCUMENTS 4,925,973  5/1990  Deweerdt et al. ............... 560/204

Primary Examiner—Jose G. Dees
Assistant Examiner—Vera C. Clarke
Attorney, Agent, or Firm—Burns, Doane, Swecker & Mathis

[57] ABSTRACT

β, γ-Unsaturated carboxylic acids, e.g., 3-hexene-1,6-dioic acid, are selectively prepared by carbonylating (with carbon monoxide) an allyl alcohol, e.g., a butenediol, at an elevated temperature and under superatmospheric pressure, in the presence of a catalytically effective amount of a palladium-based catalyst and at least one quaternary onium chloride of one of the Group VB elements nitrogen or phosphorus, such element being tetracoordinated via carbon atoms and with the proviso that such nitrogen atom may be coordinated to two pentavalent phosphorus atoms.

20 Claims, No Drawings

PREPARATION OF β, γ-UNSATURATED CARBOXYLIC ACIDS

BACKGROUND OF THE INVENTION

1. Field of the Invention

The present invention relates to the preparation of β,γ-unsaturated acids, and, more especially, to the preparation of β,γ-unsaturated acids by the carbonylation of allyl alcohols.

2. Description of the Prior Art

U.S Pat. No. 4,189,608 describes a process for preparing 3-butenoic acid by contacting allyl alcohol with carbon monoxide in the presence of a palladium chloride-based catalyst at a temperature ranging from 50° to 300° C. under high pressure, the reaction being carried out in a substantially anhydrous $C_2$–$C_{10}$ carboxylic acid as a liquid solvent.

In point of fact, the carboxylic acid is liable to react with the alcohol to produce an allyl carboxylate, which would become the reactant for the palladium-catalyzed carbonylation.

Moreover, the catalytic activity remains low, as evidenced by the relatively lengthy reaction times.

U.S. Pat. No. 4,025,547 describes the carbonylation of primary allyl alcohols into esters of the allyl vinylacetate type, in the presence of a homogeneous catalytic system containing three components:

(i) a palladium halide; with
(ii) one or more donor ligands of Group VB; and
(iii) a cocatalyst which is a halide of a Group IVB metal.

A typical example of these catalytic compositions is $PdCl_2(P(C_6H_5)_3)_2 \cdot SnCl_2$.

Triphenylphosphine, as well as tin dichloride, may be introduced, in excess.

In this process, an allyl ester is formed instead of an acid: the allyl alcohol serves both as a substrate which is carbonylated under the reaction conditions and as an esterification reagent. Moreover, the pressures employed are very high.

German Offenlegungsschrift 3,345,375 describes a process for the carbonylation of secondary or tertiary allyl alkanols in the presence of palladium halides complexed with a phosphine, where appropriate in excess, at 50°–150° C. under high pressure.

While the selectivity of the reaction appears to be appreciable, the activity of the catalytic system remains low, as evidenced both by the lengthy reaction times and the very high pressures which are employed in this process.

SUMMARY OF THE INVENTION

Accordingly, a major object of the present invention is the provision of an improved process for the preparation of β,γ-unsaturated acids by the carbonylation of allyl alcohols with enhanced efficiency, in particular under milder pressure conditions than those to date characterizing the state of this art.

Briefly, the present invention features a process for preparing β,γ-unsaturated acids by contacting an allyl alcohol, carbon monoxide and a palladium-based catalyst at high temperature and under a pressure above atmospheric pressure, and wherein the reaction is also carried out in the presence of at least one quaternary onium chloride of a Group VB element selected from between nitrogen and phosphorus, said element being tetracoordinated to carbon atoms, with the proviso that such nitrogen atom may be coordinated to two pentavalent phosphorus atoms.

DETAILED DESCRIPTION OF THE PREFERRED EMBODIMENTS OF THE INVENTION

More particularly according to the present invention, by "allyl alcohol" is intended an unsaturated mono- or dihydroxylated compound corresponding to the general formula:

in which $R^1$ to $R^5$, which may be identical or different, are each a hydrogen atom; an alkyl, aryl or aralkyl radical having at most 20 carbon atoms; an alkenyl radical devoid of terminal unsaturation and having at most 15 carbon atoms; with the proviso that any one of the radicals $R^1$ to $R^5$ can also be a hydroxymethyl radical ($-CH_2OH$), and with the further proviso that $R^1$ (or $R^2$) and $R^4$ (or $R^5$) may together form a single divalent alkylene radical having from 2 to 5 carbon atoms.

When one of the radicals $R^1$ to $R^5$ is a hydroxymethyl radical, all of the other radicals $R^1$ to $R^5$ are preferably hydrogen atoms.

The hydroxymethyl group is reactive under the conditions of the process of the invention, and it has also been found, quite surprisingly, that it is possible to prepare 3-hexene-1,6-dioic acid with appreciable selectivity from 2-butene-1,4-diol, a well as from 1-butene-3,4-diol, or mixtures thereof. It will of course be appreciated that hexene-1,6-dioic acid may be hydrogenated to adipic acid.

Adipic acid, one of the basic raw materials of nylon 66, is produced in vast amounts and, for this reason alone, any novel route for the ultimate production of such diacid and/or derivative thereof would be of significant interest to this art.

As is apparent from the general formula (I) above, primary, secondary or tertiary allyl alcohols can be used in the process of the present invention.

Exemplary of such alcohols, the following are representative:
Allyl alcohol;
2-Buten-1-ol (crotyl alcohol);
3-Buten-2-ol (1-methylallyl alcohol);
1-Penten-3-ol;
1-Hexen-3-ol:
1-Octen-3-ol;
3,7-Dimethyl-2,6-octadien-1-ol (geraniol):
3,7-Dimethyl-1,6-octadien-3-ol (linalool);
3-Phenyl-2-propen-1-ol (cinnamyl alcohol);
2-Methyl-1-propen-3-ol;
2-Cyclohexen-1-ol;
3-Methyl-1-buten-3-ol;
2-Butene-1,4-diol;
1-Butene-3,4-diol.

The process according to the present invention is carried out in the presence of a palladium-based catalyst.

Although the exact nature of the species (one or more) which is/are catalytically active in the subject reaction has not been completely elucidated, it has been determined that various palladium compounds and palladium metal are useful precursors for carrying out the process of the invention.

Exemplary sources of palladium for carrying out the process of the invention, the following are representative:

(a) palladium metal deposited, where appropriate, on a support such as charcoal, alumina or silica;

(b) $PdCl_2$, $Pd(OAc)_2$, $PBu_4PdCl_3$ (Bu=n-butyl);

(c) salts or $\pi$-allyl complexes of palladium in which the anion coordinated to the Pd cation is selected from among the following anions: carboxylates such as formate, acetate, propionate, benzoate; acetylacetonate, halides such as $Cl^-$ and $Br^-$, and preferably $Cl^-$.

The exact amount of catalyst to be employed, which can vary over wide limits, will depend above all on a compromise between the desired efficiency and the consumption of the catalyst, and on the other conditions selected for the reaction.

In general, good results are obtained using a concentration of palladium in the reaction medium ranging from $10^{-3}$ to 1 mol/l. Preferably, this concentration ranges from $2 \times 10^{-3}$ and $5 \times 10^{-2}$ mol/l.

One of the essential characteristics of the present process is that the reaction is also carried out in the presence of a quaternary onium chloride of a Group VB element selected from between nitrogen and phosphorus, such element being tetracoordinated via carbon atoms, with the proviso that such nitrogen atom may be coordinated to pentavalent phosphorus atoms.

By "quaternary onium cation in which the Group VB element is tetracoordinated to carbon atoms" are intended cations formed from nitrogen or phosphorus and from four identical or different monovalent hydrocarbon groups, the free valency of which is borne by a carbon atom, each group being bonded to the aforementioned element via the said free valency, with the proviso, moreover, that any two of these groups may together form a single divalent radical.

To advantageously carry out the process of the invention, the quaternary onium chloride comprises a quaternary cation corresponding to one of the formulae (II) to (V) below:

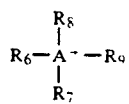  (II)

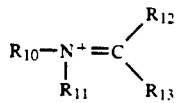  (III)

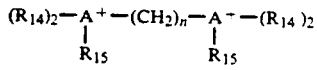  (IV)

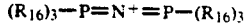  (V)

in which A is nitrogen or phosphorus; $R_6$, $R_7$, $R_8$ and $R_9$, which may be identical or different, are each a linear or branched chain alkyl radical having from 1 to 16 carbon atoms, optionally substituted by a phenyl, hydroxy, halo, nitro, alkoxy or alkoxycarbonyl group; a linear or branched chain alkenyl radical having from 2 to 12 carbon atoms, and preferably from 4 to 8 carbon atoms; an aryl radical having from 6 to 10 carbon atoms, optionally substituted by one or more alkyl radicals, having from 1 to 4 carbon atoms, or alkoxy, alkoxycarbonyl or halo radicals; with the proviso that two of said radicals $R_6$ to $R_9$ may together form a linear or branched chain alkylene, alkenylene or alkadienylene radical having from 3 to 6 carbon atoms; $R_{10}$, $R_{11}$, $R_{12}$ and $R_{13}$, which may be identical or different, are each a linear or branched chain alkyl radical having from 1 to 4 carbon atoms; with the proviso that the radicals $R_{12}$ and $R_{13}$ may together form an alkylene radical having from 3 to 6 carbon atoms; and with the further proviso that the radicals $R_{11}$ and $R_{12}$ or $R_{11}$ and $R_{13}$ may together form an alkylene, alkenylene or alkadienylene radical having 4 carbon atoms and constituting, with the N atom, a nitrogenous heterocycle; $R_{14}$ is a linear or branched chain alkyl radical having from 1 to 4 carbon atoms or a phenyl radical; $R_{15}$ is a linear or branched chain alkyl radical having from 1 to 4 carbon atoms, identical to or different from $R_{14}$; a linear or branched chain alkenyl radical having from 2 to 12 carbon atoms, and preferably from 4 to 8 carbon atoms; n is an integer not less than 1 and not more than 10, and preferably not more than 6; and $R_{16}$ is an aryl radical having from 6 to 10 carbon atoms, optionally substituted by one or more alkyl radicals having to 4 carbon atoms, or alkoxy, alkoxycarbonyl or halo groups.

Exemplary of the quaternary onium cations corresponding to the formula (II), the following cations are representative:
Tetramethylammonium;
Triethylmethylammonium;
Tributylmethylammonium;
Trimethyl(n-propyl)ammonium;
Tetraethylammonium;
Tetrabutylammonium;
Dodecyltrimethylammonium;
Methyltrioctylammonium;
Heptyltributylammonium;
Tetrapropylammonium;
Tetrapentylammonium;
Tetrahexylammonium;
Tetraheptylammonium;
Tetraoctylammonium;
Tetradecylammonium;
Butyltripropylammonium;
Methyltributylammonium;
Pentyltributylammonium;
Methyldiethylpropylammonium;
Ethyldimethylpropylammonium;
Tetradodecylammonium;
Tetraoctadecylammonium;
Hexadecyltrimethylammonium;
Benzyltrimethylammonium;
Benzyldimethylpropylammonium;
Benzyldimethyloctylammonium;
Benzyltributylammonium;
Benzyltriethylammonium;
Phenyltrimethylammonium;
Benzyldimethyltetradecylammonium;
Benzyldimethylhexadecylammonium;
Dimethyldiphenylammonium;
Methyltriphenylammonium;
(2-Butenyl)triethylammonium;
N,N-Dimethyl(tetramethylen)ammonium;
N,N-Diethyl(tetramethylen)ammonium;
Tetramethylphosphonium;
Tetrabutylphosphonium;
Ethyltrimethylphosphonium;
Trimethylpentylphosphonium;
Octyltrimethylphosphonium;

Dodecyltrimethylphosphonium;
Trimethylphenylphosphonium;
Diethyldimethylphosphonium;
Dicyclohexyldimethylphosphonium;
Dimethyldiphenylphosphonium;
Cyclohexyltrimethylphosphonium;
Triethylmethylphosphonium;
Methyltri(isopropyl)phosphonium;
Methyltri(n-propyl)phosphonium;
Methyltri(n-butyl)phosphonium;
Methyltris(2-methylpropyl)phosphonium;
Methyltricyclohexylphosphonium;
Methyltriphenylphosphonium;
Methyltribenzylphosphonium;
Methyltris(4-methylphenyl)phosphonium;
Methyltrixylylphosphonium;
Diethylmethylphenylphosphonium;
Dibenzylmethylphenylphosphonium;
Ethyltriphenylphosphonium;
Tetraethylphosphonium;
Ethyltri(n-propyl)phosphonium;
Triethylpentylphosphonium;
Hexadecyltributylphosphonium;
Ethyltriphenylphosphonium;
n-Butyltri(n-propyl)phosphonium;
Butyltriphenylphosphonium;
Benzyltriphenylphosphonium;
(β-Phenylethyl)dimethylphenylphosphonium;
Tetraphenylphosphonium;
Triphenyl(4-methylphenyl)phosphonium;
Tetrakis(hydroxymethyl)phosphonium;
Tetrakis(2-hydroxyethyl)phosphonium.

Exemplary cations corresponding to the formula (III), the following cations are representative:
N-methylpyridinium;
N-ethylpyridinium;
N-hexadecylpyridinium;
N-methylpicolinium.

Exemplary cations corresponding to the formula (IV), the following cations are representative:
1,2-Bis(trimethylammonium)ethane;
1,3-Bis(trimethylammonium)propane;
1,4-Bis(trimethylammonium)butane;
1,3-Bis(trimethylammonium)butane.

And exemplary cations corresponding to the formula (V), the following cations are representative:
Bis(triphenylphosphine)iminium;
Bis(tritolylphosphine)iminium.

Advantageously, those onion cations are used corresponding to the formula (II) above, in which:

A is phosphorus; and $R_6$, $R_7$, $R_8$ and $R_9$, which may be identical or different, are each a linear or branched chain alkyl radical having from 1 to 8 carbon atoms, or a phenyl or 4-methylphenyl radical.

A tetraalkylphosphonium chloride is preferably used.

Tetrabutylphosphonium chloride, which is readily available and particularly efficient, is more especially preferred.

It will be appreciated that certain palladium compounds, such as $PBu_4PdCl_3$ mentioned above and resulting from the reaction between equivalent molar amounts of $PBu_4Cl$ and $PdCl_2$, can constitute both a source of palladium and a means of introducing a quaternary onium chloride as described above.

It has been found that the beneficial effect provided by the presence in the carbonylation medium of a quaternary onium chloride corresponding to the definition given above is substantial at and above an onium cation/palladium mole ratio of 0.5; in particular, an especially advantageous effect has been observed when said ratio ranges from 1 to 50, it even being possible for a higher ratio to be used without adversely affecting the reaction. In effect, the quaternary onium chloride may be used in relatively large amounts and thus also serve as a diluent for the reaction medium.

The reaction is typically carried out in the liquid phase at a temperature ranging from 50° to 150° C., and preferably from 80° to 130° C., under a carbon monoxide pressure ranging from 10 to 250 bars (1,000 and 25,000 kPa), and preferably from 15 to 180 bars (1,500 and 18,000 kPa).

Inert gases such as nitrogen, argon or carbon dioxide may be present with the carbon monoxide.

Of course, the reaction may be carried out in the presence of solvents or diluents exogenous to the reaction medium, such as esters, ketones, nitriles, aromatic hydrocarbons, dimethyl sulfoxide or carboxylic acid amides.

The presence of water, even in relatively large amounts (on the order of 10 moles per mole of substrate), is not detrimental and is capable, under certain conditions, of imparting a beneficial effect on the selectivity or even the activity.

The presence of a lower alkanol can prove desirable in certain cases. Indeed, although such an alcohol cannot be considered to be inert under the reaction conditions, it may be introduced as a coreagent for esterifying the β,-unsaturated acid formed, and this will provide an alternative for, for example, isolating the desired product more conveniently in its ester form. This ester may then be hydrolyzed in known manner to recover the desired product in its acid form.

This embodiment can be more especially advantageous when the allyl alcohol involved in the reaction is a butenediol and when the alkanol used is methanol or ethanol; the alkanol/diol mole ratio may then attain approximately 10.

In a preferred embodiment of the process according to the present invention, the reaction is carried out in N-methylpyrrolidone.

The allyl alcohol concentration is not critical and can vary over wide limits.

Upon completion of the reaction or of the desired reaction time, the desired acid or diacid is recovered by any suitable means, for example by extraction.

In order to further illustrate the present invention and the advantages thereof, the following specific examples are given, it begin understood that same are intended only as illustrative and in nowise limitative.

EXAMPLES 1 to 8

Control Experiments (a) to (c)

A series of experiments was carried out according to the procedure described with reference to Example 1.

The following materials were introduced into a 125-cm³ Hastelloy B2 stainless steel autoclave purged beforehand with argon:

(i) 4.4 g (50 mmol) of 2-butene-1,4-diol;
(ii) 1 mg-at. of palladium in the form of $PdCl_2$;
(iii) 5 g of $PBu_4Cl$ (17 mmol); and
(iv) 25 cm³ of acetonitrile.

The autoclave was hermetically sealed, placed in an oven having an agitator and connected to a supply of gas under pressure. The reactor was purged in the cold state with carbon monoxide and heated to 100° C.; the pressure was then adjusted to 125 bars. After 6 hours of reaction (except where otherwise indicated) the autoclave was cooled and degassed.

The reaction solution was diluted to 100 cm³ by adding solvent.

An aliquot portion was esterified with methanol and then analyzed by gas chromatography.

All of the experiments corresponded to a degree of conversion of 100%, and formation of the following various acids was observed:

HD:mixture of 3-hexene- and 2-hexenedioic acids, in which 3-hexenedioic aid was the preponderant.

$C_5ac.$:mixture of valeric, 2-methylbutyric, 3-pentenoic, 2-pentenoic and 4-pentenoic acids, in which 3-pentenoic acid was the preponderant.

$Sat.C_6$:mixture of ethylsuccinic, methylglutaric and adipic acids, in which methylglutaric acid was the preponderant.

PDO:pentadienoic acid of which the number of moles formed per 100 moles of butenediol introduced is reported for each group.

The particular conditions, as well as the results obtained, are reported in Table I below:

TABLE I:

| Example No. | Additive Nature | mmol | Solvent | t(h) | Results (%) HD | $C_5ac.$ | $Sat.C_6$ | PDO |
|---|---|---|---|---|---|---|---|---|
| a | — | 0 | $CH_3CN$ | | <2 | 60 | 16 | 1 |
| b | $PPh_3$ | 2 | $CH_3CN$ | | 2 | 0 | 0 | 15 |
| 1 | $PBu_4Cl$ | 17 | $CH_3CN$ | 3 | 37 | 28 | 9 | 0.5 |
| 2 | $PMe_4Cl$ | 17 | $CH_3CN$ | | 19 | 21 | 6 | ND |
| 3 | $PPh_4Cl$ | 17 | $CH_3CN$ | | 39 | 30 | 12 | ND |
| 4 | $NBu_4Cl$ | 17 | $CH_3CN$ | | 30 | 30 | 14 | ND |
| c | $PBu_4Br$ | 17 | $CH_3CN$ | | 4 | 48 | 15 | ND |
| 5* | $PBu_4Cl$ | 17 | NMP | 1 | 80 | 4 | 3 | 0 |
| 6* | $PBu_4Cl$ | 34 | NMP | 2 | 85 | 4 | 1 | 0.5 |
| 7* | $PBu_4Cl$ | 68 | NMP | 1.5 | 92 | 3 | 1 | 0 |
| 8 | $PBu_4Cl$ | 102 | None | 1.5 | 85 | 3 | 0.5 | 0 | t(h): absorption time if less than 6 hours
NMP: N-methylpyrrolidone
*($PBu_4Cl$ + NMP) = 30 ml
ND: not determined

EXAMPLES 9 to 11

In the autoclave and according to the procedure described above for Example 1, a second series of experiments was carried out, replacing a portion of the 2-butene-1,4-diol by an equivalent volume of solvent, maintaining the total volume (solvent+butenediol) constant and equal to 30 cm³. The particular conditions, as well as the results obtained, are reported in Table II below:

TABLE II:

| Example No. | Butenediol mmol | Solvent | t (h) | Results (%) HD | $C_5ac.$ | $Sat.C_6$ | PDO |
|---|---|---|---|---|---|---|---|
| 1 | 50 | $CH_3CN$ | 3 | 37 | 28 | 9 | 0.5 |
| 9 | 25 | $CH_3CN$ | | 53 | 18 | 13 | 0.5 |
| 5 | 50 | NMP | 1 | 80 | 4 | 3 | 0 |
| 10 | 25 | NMP | 1 | 85 | 4 | 2 | 0 |
| 11 | 100 | NMP | | 75 | 2 | 1 | 2.5 | t(h): absorption time if less than 6 hours
NMP: N-methylpyrrolidone

EXAMPLE 12 the procedure of Example 1 was repeated, but replacing palladium chloride by an equivalent amount of palladium int he form of $Pd(OAc)_2$.

After 6 hours of reaction, the following result was obtained:
HD:24%.

EXAMPLE 13

The procedure of Example 1 was repeated, but replacing palladium chloride by an equivalent amount of palladium in the form of $Pd(dba)_2$.

After 6 hours of reaction, the following result was obtained:
HD:32%.

EXAMPLE 14

The procedure of Example 1 was repeated, but using an equivalent volume of dimethyl sulfoxide as a solvent.

After 6 hours of reaction, the following result was obtained:
HD:70%.

EXAMPLE 15

The procedure of Example 1 was repeated, but using an equivalent volume of dimethylformamide as a solvent.

After 6 hours of reaction, the following result was obtained:
HD:50%.

EXAMPLE 16

The procedure of Example 5 was repeated, but replacing palladium chloride by an equivalent amount of palladium in the form of $Pd(OAc)_2$.

After 6 hours of reaction, the following result was obtained:
HD:45%.

EXAMPLE 17

The procedure of Example 5 was repeated, but replacing palladium chloride by an equivalent amount of palladium in the form of $Pd(dba)_2$.

After 21 hours of reaction, the following result was obtained:
HD:85%.

EXAMPLE 18

The procedure of Example 5 was repeated, but using 0.5 mg-at. of palladium (in the form of $PdCl_2$).

After 1 h, 30 min, absorption had finished and substantially the same results were obtained:
HD:75%.

EXAMPLE 19

The procedure of Example 5 was repeated, but using 0.12 mg-at. of palladium (in the form of $PdCl_2$).

After 12 h, absorption had finished and substantially the same results were obtained:
HD:75%.

EXAMPLE 20

The procedure of Example 5 was repeated, but using an equivalent amount of 1-butene-3,4-diol.

Substantially the same results were obtained:
HD:80%.

EXAMPLE 21

The procedure of Example 5 was repeated, but replacing palladium chloride by an equivalent amount of palladium deposited on charcoal (3% by weight of Pd on C).

After 1 hour, absorption had finished and the following was result was obtained:
HD:44%.

EXAMPLE 22

The procedure of Example 5 was repeated, but replacing palladium chloride by an equivalent amount of $PBu_4PdCl_3$ and replacing $PBu_4Cl$ by an equivalent volume of N-methylpyrrolidone.

After 15 min, absorption had finished and the following result was obtained:
HD:45%.

EXAMPLES 23 to 27

A series of experiments similar to Example 5 above was carried out, but replacing N-methylpyrrolidone (NMP) by the same volume of an (NMP+water) or (NMP+methanol) mixture.

The particular conditions and the results obtained are reported in Table III below:

TABLE III:

| Example No | Water (mmol) | Methanol (mmol) | t | HD % |
|---|---|---|---|---|
| 23 | 50 | — | 40 min | 74.5 |
| 24 | 100 | — | 6 h | 85 |
| 25 | 200 | — | 1 h | 78 |
| 26 | — | 100 | 1 h | 78 |
| 27 | — | 200 | 50 min | 70 | t: absorption time

EXAMPLES 28 to 38

A series of experiments was carried out on a charge similar to that described in Example 1, using as a solvent either acetonitrile (Examples 28 to 32) or N-methylpyrrolidone (NMP) (Examples 33 to 38), modifying the reaction temperature (T° C.) or the carbon monoxide pressure measured at temperature {P(CO)}.

The particular conditions and the results obtained are reported in Table IV below.

TABLE IV:

| Example No. | P(CO) bars | T °C. | t (h) | Results (%) | | | |
|---|---|---|---|---|---|---|---|
| | | | | HD | C$_5$ac. | Sat.C$_6$ | PDO |
| 28 | 60 | 100 | 4.5 | 20 | 28 | 12 | 0 |
| 29 | 120 | 100 | 3 | 41 | 18 | 15 | 0 |
| 30 | 180 | 100 | 3 | 44 | 13 | 2 | 0 |
| 31 | 120 | 130 | 3 | 18 | 30 | 13 | 1 |
| 32 | 120 | 70 | | 43 | 5 | 2 | 2 |
| 33 | 15 | 100 | (*) | 15 | 46 | 2 | |
| 34 | 30 | 100 | | 56 | 17 | 3 | 1.5 |
| 35 | 60 | 100 | 2 | 80 | 6 | 1 | 2 |
| 5 | 120 | 100 | 1 | 80 | 4 | 3 | 0 |
| 36 | 180 | 100 | 2 | 82 | 2 | 0 | 3 |
| 37 | 120 | 130 | 0.66 | 55 | 14 | 2 | 2 |
| 38 | 120 | 70 | | 70 | 1 | 0 | 5 | t(h): absorption time if less than 6 hours
NMP: N-methylpyrrolidone
(*): absorption time = 18 hours

EXAMPLE 39

In an apparatus and according to a procedure similar to that described above, an experiment was carried out on a charge consisting of:
(i) 50 mmol of allyl alcohol;
(ii) 37.5 cm$^3$ of ethylbenzene;
(iii) 0.25 mg-at. of palladium introduced in the form of $PdCl_2$;
(iv) 2.5 mmol of $PBu_4Cl$.

The temperature was 80° C. and the pressure adjusted to 200 bars. After 6 hours of reaction, the autoclave was cooled and degassed.

Analysis of the crude mixture by gas chromatography evidenced that the degree of conversion of allyl alcohol was 100%, and that the mixture contained allyl vinylacetate (RY=60%; RY being defined by the ratio of twice the number of moles of vinylacetate detected to the number of moles of allyl alcohol introduced) and 3-butenoic acid, the amount of which, estimated as follows, was on the order of 30% relative to the allyl alcohol introduced.

The estimation was carried out by the difference between, on the one hand the total amount of methyl ester assayed by gas chromatography after esterification, and, on the other, the amount of methyl ester resulting from degradation of the allyl vinylacetate, analysis of the mixture, after esterification, by gas chromatography having provided the following results:
RY (allyl vinylacetate)=20%
RY (methyl 3-butenoate)=50%
(RY:molar yield relative to the substrate introduced).

Control Experiment (d)

The procedure of Example 39 was repeated, but introducing an equivalent amount of palladium in the form of the complex:

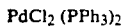

and replacing $PBu_4Cl$ by an equivalent amount of $SnCl_2.H_2O$.

The results obtained, all conditions otherwise being equal, were as follows:
Analysis of the crude mixture:
Degree of conversion of allyl alcohol:15%
RY (allyl vinylacetate):16%.
Analysis of the mixture after esterification:
RY (allyl vinylacetate):8%
RY (methyl 3-butenoate):6%.

Comparison of the results obtained in Example 39 (according to the invention) and in control experiment (d), respectively, demonstrated the fact that, with the process according to the invention, a novel route was provided for the β,γ-unsaturated acid, and with an improved efficiency of carbonylation.

EXAMPLE 40

In an apparatus and according to a procedure similar to that described above, an experiment was carried out on a charge consisting of:
(i) 40 mmol of allyl alcohol;
(ii) 25 cm³ of N-methylpyrrolidone;
(iii) 1 mmol of PcDl₂;
(iv) 17 mmol of PBu₄Cl.

The temperature was 100° C. and the pressure adjusted to 120 bars. After 30 min of reaction (absorption time), the results obtained were as follows:
Analysis of the crude mixture:
Degree of conversion of allyl alcohol:100%
RY (allyl vinylacetate):0%
Analysis of the mixture after esterification:
RY (allyl vinylacetate):0%
RY (methyl 3-butenoate):62%.

This example evidenced that the β,τ-unsaturated acid was formed selectively, and with an appreciable efficiency of carbonylation.

EXAMPLE 41

The procedure of Example 40 was repeated, but adding 100 mmol of water to the charge. After 10 minutes of reaction (absorption time), the results obtained were as follows:
Analysis of the crude mixture
Degree of conversion of allyl alcohol:100%
RY (allyl vinylacetate):2%.
Analysis of the mixture after esterification:
RY (allyl vinylacetate):0%
RY (methyl 3-butenoate):100%.

Control Experiment (e)

The procedure of Example 40 above was repeated, but replacing palladium chloride by an equivalent amount of the complex PdCl₂(PPh₃)₂ and PBu₄Cl by 10 mmol of SnCl₂.2H₂O. After 4 hours of reaction (absorption time), the results obtained were as follows:
Analysis of the crude mixture:
Degree of conversion of allyl alcohol:10%
RY (allyl vinylacetate):2%.
Analysis of the mixture after esterification:
RY (allyl vinylacetate):0%
RY (methyl 3-butenoate):5%.

EXAMPLES 42 to 46

In an autoclave and according to the procedure described above, a series of experiments was carried out starting with various allyl alcohols under the following common condition:
The charge consisted of:
(i) 50 mmol of alcohol, the nature of which is indicated in Table V below;
(ii) 1 mg-at. of palladium in the form of PdCl₂;
(iii) 17 mmol of PBu₄Cl;
(iv) 25 cm³ of N-methylpyrrolidone.

The reaction temperature was 100° C. and the carbon monoxide pressure measured at temperature was 120 bars.

Upon completion of the reaction, the crude reaction mixture was analyzed by gas chromatography and was then esterified with methanol; the amount of β,γ-unsaturated acid was determined by gas chromatographic assay of the corresponding methyl esters.

DC:represents the degree of conversion of the alcohol in question.
RY:represents the number of moles of β,-unsaturated acid formed per 100 moles of alcohol introduced.

TABLE V:

| Example No. | Nature of the alcohol | t(h) | DC | RY |
|---|---|---|---|---|
| 42 | 2-Methyl-1-propen-3-ol | 3.5 | 90 | 50 |
| 43 | 2-Buten-1-ol | 3.5 | 100 | 92 |
| 44 | 2-Cyclohexen-1-ol | 3.5 | 100 | 82 |
| 45 | 3-Phenyl-2-propen-1-ol | 1 | 92 | 85 |
| 46 | 3-Methyl-1-buten-3-ol | 0.5 | 100 | 100 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a β,τ-unsaturated acid, comprising contacting allyl alcohol, carbon monoxide and a catalytically effective amount of a palladium-based catalyst at elevated temperature effective to carbonylate said allyl alcohol and under superatmospheric pressure, in the presence of at least one quaternary onium chloride of one of the Group VB elements nitrogen or phosphorus, such element being tetracoordinated via carbon atoms and with the proviso that the nitrogen atom may be coordinated to two pentavalent phosphorus atoms.

2. The process as defined by claim 1, said allyl alcohol having the formula (I):

in which R¹ to R⁵, which may be identical or different, are each a hydrogen atom; an alkyl, aryl or aralkyl radical having at most 20 carbon atoms; an alkenyl radical devoid of terminal unsaturation and having at most 15 carbon atoms; with the proviso that any one of the radicals R¹ to R⁵ can also be hydroxymethyl radical (—CH₂OH), and with the further proviso that R¹ and R⁴ or R² and R⁵ may together form a single divalent alkylene radical having from 2 to 5 carbon atoms.

3. The process as defined by claim 1, said quaternary onium chloride comprising a quaternary onium cation having one of the formulae (II) to (V) below:

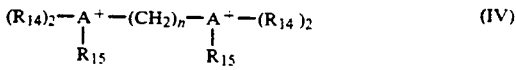

-continued $$(R_{16})_3-P=N^+=P-(R_{16})_3 \quad (V)$$

in which formulae A is nitrogen or phosphorus; $R_6$, $R_7$, $R_8$ and $R_9$, which may be identical or different, are each a straight-chain or branched alkyl radical having from 1 to 16 carbon atoms, or substituted by a phenyl, hydroxyl, halogeno, nitro, alkoxy or alkoxycarbonyl substituent; an straight-chain or branched alkenyl radical having from 2 to 12 carbon atoms; an aryl radical having 6 to 10 carbon atoms, or substituted by one or more alkyl radicals having from 1 to 4 carbon atoms, or alkoxy, alkoxycarbonyl or halogeno substituents; with the proviso that two of said radicals $R_6$ to $R_9$ may together form a straight-chain or branched alkylene, alkenylene or alkadienylene radical having from 3 to 6 carbon atoms; $R_{10}$, $R_{11}$, $R_{12}$ and $R_{13}$, which may be identical or different, are each a straight-chain or branched alkyl radical having from 1 to 4 carbon atoms; with the proviso that the radicals $R_{12}$ and $R_{13}$ may together form an alkylene radical having from 3 to 6 carbon atoms; and with the further proviso that the radicals $R_{11}$ and $R_{12}$ or $R_{11}$ and $R_{13}$ may together form an alkylene, alkenylene or alkadienylene radical having 4 carbon atoms and forming, with the N atom, a nitrogen-containing heterocyclic radical; $R_{14}$ is a straight-chain or branched alkyl radical having from 1 to 4 carbon atoms or a phenyl radical; $R_{15}$ is a straight-chain or branched alkyl radical having from 1 to 4 carbon atoms, identical to or different from $R_{14}$; or a straight-chain or branched alkenyl radical having from 2 to 12 carbon atoms; n is an integer greater than or equal to 1 and less than or equal to 10; and $R_{16}$ is an aryl radical having 6 to 10 carbon atoms, or substituted by one or more alkyl groups having from 1 to 4 carbon atoms, or alkoxy, alkoxycarbonyl or halogeno substituents.

4. The process as defined by claim 3, said quaternary onium cation having the formula (II), in which:
A is phosphorus; and
$R_6$, $R_7$, $R_8$ and $R_9$, which may be identical or different, are each a linear or branched chain alkyl radical having from 1 to 8 carbon atoms, or a phenyl or 4-methylphenyl radical.

5. The process as defined by claim 1, said quaternary onium chloride comprising tetrabutylphosphonium chloride.

6. The process as defined by claim 1, wherein the mole ratio of the onium cation to palladium is not less than 1.

7. The process as defined by claim 1, wherein the concentration of palladium in the reaction medium ranges from $10^{-3}$ to 1 mol/l.

8. The process as defined by claim 1, carried out at a reaction temperature ranging from 50° to 150° C.

9. The process as defined by claim 1, carried out under a pressure ranging from 10 to 250 bars.

10. The process as defined by claim 1, carried out in the presence of an organic diluent or solvent.

11. The process as defined by claim 10, carried out in the presence of an N-methylpyrrolidone reaction solvent.

12. The process as defined by claim 10, carried out in the presence of a reaction solvent comprising the quaternary onium chloride.

13. The process as defined by claim 1, said allyl alcohol comprising 2-butene-1,4-diol, 1-butene-3,4-diol, or admixture thereof.

14. The process as defined by claim 1, carried out in the presence of a lower alkanol.

15. The process as defined by claim .1, carried out in the presence of water.

16. The process as defined by claim 8, carried out at a temperature ranging from 80° to 130° C.

17. The process as defined by claim 9, carried out under a pressure ranging from 15 to 180 bars.

18. The process as defined by claim 3, said quaternary onium cation having the formula (III).

19. The process as defined by claim 3, said quaternary onium cation having the formula (IV).

20. The process as defined by claim 3, said quaternary onium cation having the formula (V).

* * * * *